United States Patent [19]

Saito et al.

[11] Patent Number: 5,214,065

[45] Date of Patent: May 25, 1993

[54] DC-89 DERIVATIVES

[75] Inventors: Hiromitsu Saito, Sagamihara; Akira Asai, Fujisawa; Satoru Nagamura, Machida; Eiji Kobayashi, Numazu; Katsushige Gomi, Susono, all of Japan

[73] Assignee: Kyowa Hakko Kogyo Co., Ltd., Tokyo, Japan

[21] Appl. No.: 710,407

[22] Filed: Jun. 5, 1991

[30] Foreign Application Priority Data

Jun. 11, 1990 [JP] Japan .................. 2-152098

[51] Int. Cl.$^5$ .................. A61K 31/405; C07D 487/04
[52] U.S. Cl. ........................... 514/411; 540/480; 540/602; 544/359; 546/271; 548/429
[58] Field of Search ............... 548/431, 433; 514/411

[56] References Cited

U.S. PATENT DOCUMENTS

| | | | |
|---|---|---|---|
| 4,169,888 | 10/1979 | Hanka et al. | 424/121 |
| 4,912,227 | 3/1990 | Kelly et al. | 548/421 |

FOREIGN PATENT DOCUMENTS

| | | |
|---|---|---|
| 0154445 | 9/1985 | European Pat. Off. . |
| 0271581 | 6/1988 | European Pat. Off. . |
| 0318056 | 5/1989 | European Pat. Off. . |
| 0339681 | 11/1989 | European Pat. Off. . |
| 0351865 | 1/1990 | European Pat. Off. . |
| 0354583 | 2/1990 | European Pat. Off. . |
| 0365041 | 4/1990 | European Pat. Off. . |
| 0406749 | 1/1991 | European Pat. Off. . |
| WO88/04659 | 6/1988 | PCT Int'l Appl. . |
| 8804659 | 6/1988 | PCT Int'l Appl. . |

OTHER PUBLICATIONS

Jpn J. Cancer Research 80, 686-689, 1989.
Yasuzawa et al., "Chem. and Pharm. Bull.", vol. 36, No. 9 pp. 3728-3731 (1988).

*Primary Examiner*—Munkund J. Shah
*Assistant Examiner*—Y. N. Gupta
*Attorney, Agent, or Firm*—Fitzpatrick, Cella, Harper & Scinto

[57] ABSTRACT

Novel DC-89 derivatives have an excellent anti-tumor activity, and thus are useful as anti-tumor agent.

5 Claims, No Drawings

DC-89 DERIVATIVES

BACKGROUND OF THE INVENTION

The present invention relates to DC-89 derivatives. The compounds have an excellent anti-tumor activity and are useful as anti-tumor agents.

As compounds structurally similar to the DC-89 derivatives of the present invention, those represented by the following structure are known.

DC-89A1: V = —CH$_2$—, T = Cl
DC-89A2: V = single bond, T = CH$_2$Cl
DC-89B1: V = —CH$_2$—, T = Br
DC-89B2: V = single bond, T = CH$_2$Br DC-89A1 is disclosed in EP0271581A1; DC-89A2, DC-89B1 and DC-89B2 are disclosed in EP0351865A2, SF2582A and SF2582B having the same structures as those of DC-89A2 and DC-89A1 are disclosed in EP0318056A2 and SF2582C derivatives having a similar structure are disclosed in EP0339681A2, DC-88A having a structure similar to the compounds of the present invention is disclosed in EP0271581A1. DC-88A not only shows an antibacterial activity against a variety of bacteria but also exhibits an anti-tumor activity against melanoma B-16, etc. DC-88A has the following structure.

Furthermore, DC-88A derivatives are disclosed in EP-0354583A1 and EP-0365041A1. CC-1065 having a structure similar to DC-88A is an anti-tumor agent, and its derivatives are disclosed in U.S. Pat. No. 4,169,888, U.S. Pat. No. 4,912,227 and WO 88/04659.

SUMMARY OF THE INVENTION

An object of the present invention is to provide DC-89 derivatives having an excellent anti-tumor activity.

The present invention relates to DC-89 derivatives represented by general formula (A):

wherein L represents chlorine or bromine; R represents R$^1$R$^2$ (wherein each of R$^1$ and R$^2$ independently represents hydrogen, lower alkyl or phenyl), (wherein n represents an integer of 4 to 7) or (wherein Y represents oxygen or N-M in which M represents lower alkyl); X represents a member selected from the group consisting of (a), (b), (c), (d) and (e).

(a)

wherein each of X$^1$ and X$^2$ independently represents hydrogen; OR$^3$ (wherein R$^3$ represents lower alkyl); NHCO$_2$R$^3$ (wherein R$^3$ has the same significance as described above); or NR$^4$R$^5$ (wherein each of R$^4$ and R$^5$ independently represents hydrogen or lower alkyl); and Z represents NH or oxygen;

(b)

wherein m represents 1 or 2; and X$^1$ and X$^2$ have the same significance as described above;

(c)

wherein X$^1$ and X$^2$ have the same significance as described above;

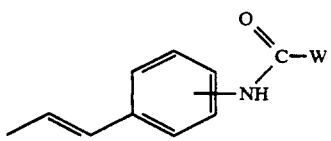

wherein W represents (a) or (b); and (a) and (b) have the same significance as described above.

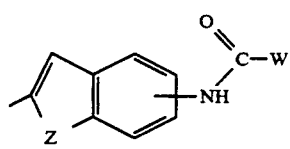

wherein W and Z have the same significance as described above; or a pharmaceutically acceptable salt thereof.

DETAILED DESCRIPTION OF THE INVENTION

Hereafter, the compounds represented by general formula (A) are referred to as Compound (A). Similarly, the compounds represented by general formulas (I), (II), (III) . . . are referred to as Compounds (I), (II), (III) . . . , respectively. Compounds (IVa) and (VIb) mean that these compounds are included in Compound (IV) and Compound (VI), respectively.

In the definition of the respective groups in general formula (A), lower alkyl includes the straight or branched alkyl having 1 to 6 carbon atoms such as methyl, ethyl, propyl, isopropyl, butyl, isobutyl, sec-butyl, tert-butyl, pentyl, neopentyl, hexyl, etc.

As the pharmaceutically acceptable salts of Compound (A), mention may be made of inorganic acid addition salts such as hydrochlorides, hydrobromides, hydroiodides, nitrates, sulfates and phosphates; organic acid addition salts such as acetates, benzoates, maleates, fumarates, tartarates, succinates, citrates, oxalates, glyoxylates, aspartates, methanesulfonates, etc.

Next, the process for preparing Compound (A) is explained below.

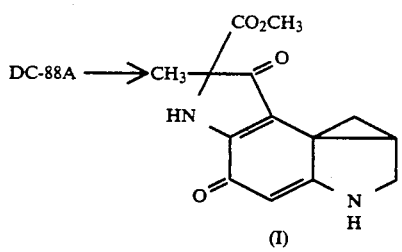

DC-88A is treated with a base in an inert solvent to give Compound (I). As the base, mention may be made of sodium methoxide, sodium hydroxide, potassium hydroxide, potassium t-butoxide, triethylamine, 1,8-diazabicycloundecene (DBU), potassium carbonate, etc. The base is used generally in 1 to 3 equivalents based on DC-88A. As the inert solvent, water, methanol, tetrahydrofuran (THF), dioxane, acetonitrile, etc. may be used singly or as admixture. The reaction is generally carried out at −20° to 50° C. and completed in 30 minutes to 5 hours.

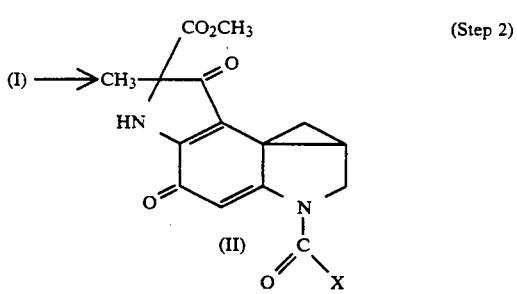

(wherein X has the same significance as described above).

Compound (II) can be obtained by reacting Compound (I) with reactive derivatives of carboxylic acid (VII) denoted by X-COOH (wherein X has the same significance as described above) in an inert solvent in the presence of a base. As the base, mention may be made of sodium hydride, lithium diisopropylamide, potassium t-butoxide, triethylamine, 4-dimethylaminopyridine, etc. The base is used generally in 1 to 2 equivalents based on Compound (I). As the inert solvent, dimethylformamide, THF, toluene, dimethylsulfoxide, etc. may be used singly or as admixture. The reactive derivatives of Compound (VII) include acid chlorides and activated esters, for example, p-nitrophenyl esters, 2,4,5-trichlorophenyl esters, N-oxysuccinimide esters, etc. The reactive derivatives are used generally in 1 to 2 equivalents based on Compound (I). The reaction is generally carried out at −50° to 30° C. and completed in 30 minutes to one day.

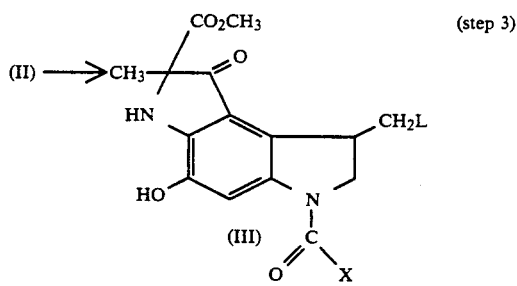

(wherein X and L have the same significance as described above).

Compound (III) is obtained by reacting Compound (II) with hydrochloric acid or hydrobromic acid. Hydrochloric acid or hydrobromic acid is used generally in 1 to 20 equivalents based on Compound (II). As the inert solvent, water, dimethylformamide, THF, toluene, dioxane, acetonitrile, etc. may be used singly or as admixture. The reaction is generally carried out at −20° to 50° C. and completed in 10 minutes to an hour.

Furthermore, Compound (III) may also be obtained by adding hydrochloric acid or hydrobromic acid to the reaction solution without isolating Compound (II) in Step 2.

(Step 4-1)

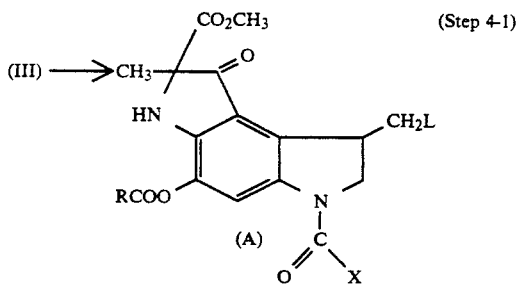

(wherein L, R and X have the same significances as described above).

Compound (A) is obtained by reacting Compound (III) with Compound (IV) shown by:

$$R^1R^2NCOCl$$

(wherein $R^1$ and $R^2$ have the same significance as described above);

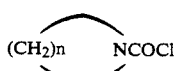

(wherein n has the same significance as described above); or

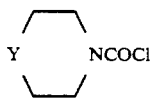

(wherein Y has the same significance as described above); in an inert solvent in the presence of a base. As the base, mention may be made of triethylamine, pyridine, 4-dimethylaminopyridine, etc. The base is used generally in 1 to 5 equivalents based on Compound (III). The base may also be used as a solvent. When the base is used as a solvent, it is used in a larger excess. As the inert solvent, pyridine, methylene chloride, dimethylformamide, THF, toluene, etc. may be used singly or as admixture. Compound (IV) is used generally in 1 to 5 equivalents based on Compound (III). The reaction is generally carried out at $-10°$ to $50°$ C. and completed in 30 minutes to one day.

Compound (A) may also be obtained from Compound (III) according to the following Step 4-2.

(Step 4-2)

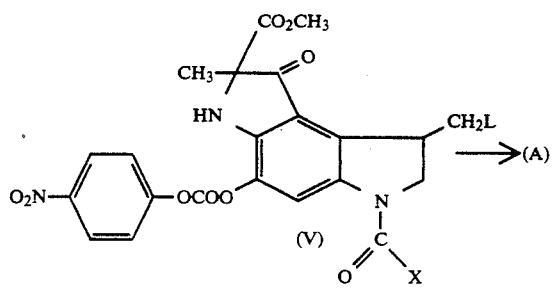

(wherein X and L have the same significance as described above).

Compound (V) can be obtained by reacting Compound (III) with p-nitrophenyl chloroformate in an inert solvent in the presence of a base. As the base, mentioned may be made of triethylamine, pyridine, 4-dimethylaminopyridine, etc. The base is used generally in 1 to 5 equivalents based on Compound (III). The base may also be used as a solvent. When the base is used as a solvent, it may be used in a larger excess. As the inert solvent, pyridine, methylene chloride, dimethylformamide, THF, toluene, etc. may be used singly or as admixture. p-Nitrophenyl chloroformate is used generally in 1 to 5 equivalents based on Compound (III). The reaction is generally carried out at $-10°$ to $50°$ C. and completed in 30 minutes to one day.

Then, Compound (V) is reacted with Compound (VI) represented by a member selected from the group consisting of:

$$R^1R^2NH$$

(wherein $R^1$ and $R^2$ have the same significance as described above);

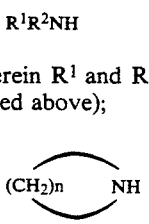

(wherein n has the same significance as described above); and

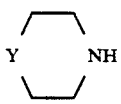

(wherein Y has the same significance as described above); to give Compound (A).

Compound (VI) is used generally in 1 to 5 equivalents based on Compound (V). The reaction is generally carried out at $-10°$ to $50°$ C. and completed in 30 minutes to one day.

After the reaction in each step is completed, water, an acid or a buffer is added to the reaction solution, if necessary, followed by extraction with a non-aqueous solvent such as ethyl acetate, chloroform, ether, etc. The extract is washed with water and aqueous sodium chloride and the extract is dried over anhydrous sodium sulfate, etc. The solvent is evaporated, and the resulting residue is subjected to silica gel column chromatography, thin layer chromatography, high performance liquid fractional chromatography, recrystallization, etc. to thereby effect purification. The intermediates may be provided to the subsequent reaction without particularly purifying them.

Compound (A) and its pharmaceutically acceptable salts may also be present in the form of addition products to water or various solvents. These addition products are also included in the present invention. Furthermore, Compound (A) includes all possible steric isomers including its optical isomers and a mixture thereof.

Structures and compound numbers of representative compounds which fall within Compound (A) are shown in Table 1.

Structures and compound numbers of the compounds synthesized in Reference Examples are shown in Tables 2 and 3.

TABLE 1

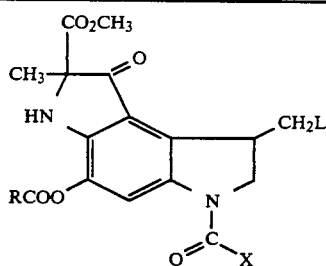

| Compound No. | R | X | L |
|---|---|---|---|
| 1 | (CH₃)₂N | 4-methoxyphenyl-propenyl | Br |
| 2 | (CH₃)₂N | 4-(NHCO₂CH₃)phenyl-propenyl | Br |
| 3 | (CH₃)₂N | 2-methyl-1H-indol-5-yl-NHC(O)-benzofuran-2-yl | Br |
| 4 | (CH₃)₂N | 3,4-dimethoxyphenyl-pentadienyl | Br |
| 5 | (CH₃)₂N | 4-(propenyl)phenyl-NHC(O)-benzofuran-2-yl | Br |
| 6 | (CH₃)₂N | 2-ethoxy-4-methoxyphenyl | Br |
| 7 | 4-methylpiperazin-1-yl | 4-methoxyphenyl-propenyl | Br |
| 8 | piperidin-1-yl | 4-methoxyphenyl-propenyl | Br |
| 9 | morpholin-4-yl | 4-methoxyphenyl-propenyl | Br |

TABLE 1-continued
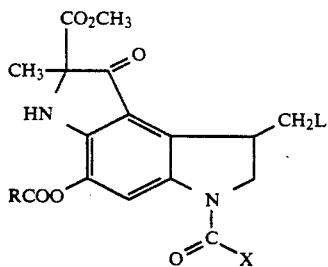
| Compound No. | R | X | L |
|---|---|---|---|
| 10 | (CH₃)₂N | 2-methyl-5-(NHCO₂CH₃)-1H-indol-yl | Br |
| 11 | (CH₃)₂N | (E)-propenyl-C₆H₄-N(CH₃)₂ | Br |
| 12 | (CH₃)₂N | (E)-propenyl-C₆H₄-OCH₃ | Cl |
| 13 | (CH₃)₂N | (E)-propenyl-C₆H₄-N(CH₃)₂ | Cl |
| 14 | 4-methylpiperazin-1-yl | (E)-propenyl-C₆H₄-OCH₃ | Cl |
| 15 | (CH₃)₂N | (E)-propenyl-C₆H₄-NHCH₃ | Br |
| 16 | (CH₃)₂N | 2-methyl-5-methoxybenzofuran-yl | Br |
| 17 | (CH₃)₂N | (E)-propenyl-3-NH₂-4-OCH₃-C₆H₃ | Br |

TABLE 2
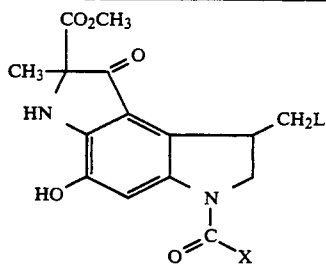
| Compound No. | X | L |
|---|---|---|
| b | 4-methoxy-(prop-1-enyl)benzene | Br |
| c | 4-(NHCO₂CH₃)-(prop-1-enyl)benzene | Br |
| e | 5-amino-2-methylindole | Br |
| f | 2-methyl-5-[NHCO-CH=CH-(2-methoxyphenyl)]indole | Br |
| g | 3,4-dimethoxy-(penta-1,3-dienyl)benzene | Br |
| h | 4-(prop-1-enyl)phenyl-NHCO-(1H-indol-2-yl) | Br |
| i | 4-methoxy-(2-ethoxy)benzene | Br |
| j | 5-(NHCO₂CH₃)-2-methylindole | Br |
| k | 4-N(CH₃)₂-(prop-1-enyl)benzene | Br |

TABLE 2-continued

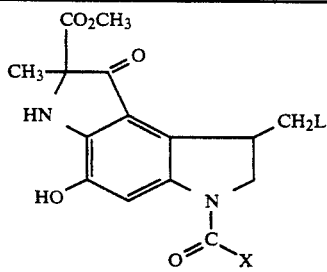

| Compound No. | X | L |
|---|---|---|
| l | ⟨phenyl-OCH₃ with propenyl⟩ | Cl |
| m | ⟨phenyl-N(CH₃)₂ with propenyl⟩ | Cl |

TABLE 3

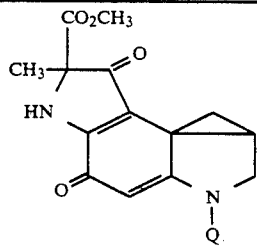

| Compound No. | Q |
|---|---|
| a | H |
| d | ⟨2-acetyl-6-(NHCO₂C(CH₃)₃)-indole⟩ |

Next, pharmacological activity of representative Compound (A) is explained by referring to Test Example.

Test Example

Therapeutic effect against sarcoma 180 tumor

Sarcoma 180 cells of $5 \times 10^5$ were subcutaneously implanted into each male ddY mouse of a group consisting of 5 mice at the axilla. One day after the transplantation, 0.2 ml of physiological saline containing Compound (A) in concentrations as shown in Table 4 was intravenously administered to mice. Seven days after the implantation, T/C [T: mean volume (mm³) of tumor in the test group, C: mean volume (mm³) of tumor in the control group (0.2 ml of physiological saline was intravenously administered)] was determined.

The results are shown in Table 4.

TABLE 4

| Compound No. | Dose (mg/kg) | T/C |
|---|---|---|
| 1 | 16 | 0.078 |
| 1 | 8 | 0.23 |
| 3 | 0.5 | 0.34 |
| 5 | 4 | 0.16 |
| 10 | 4 | 0.13 |
| 11 | 16 | 0.086 |
| 11 | 8 | 0.092 |
| 15 | 16 | 0.055 |
| 16 | 1.0 | 0.13 |

Compound (A) can be used as an anti-tumor agent, singly or in combination with at least one pharmaceutically acceptable auxiliary agent. For example, Compound (A) is dissolved in physiological saline or an aqueous solution of glucose, lactose, mannitol, etc. to prepare an appropriate pharmaceutical composition which is suitable for an injection. Otherwise, Compound (A) or its salts are freeze-dried in a conventional manner and sodium chloride is added thereto to prepare an injection powder. If necessary and desired, the pharmaceutical composition may also contain additives well known in the art of preparations, for example, pharmaceutically acceptable salts, etc. A dose of Compound (A) may vary depending upon age, condition, etc. of patient, and is administered to mammal, generally in a dose of 0.01 to 50 mg/kg/day. The composition containing Compound (A) is intravenously administered, for example, once a day (single administration or consecutive daily administration) or intermittently, 1 to 3 times a week or once per 2 to 3 weeks. If desired, the composition may also be administered intraarterially, intraperitoneally, intrathoracically, etc. in a similar dose and administration mode. If desired, the composition may also be administered orally, in a similar dose and administration mode. Mode of oral administration includes tablets, capsules, powders, granulates, ampoules, etc. and these preparations may also contain pharmaceutical aids well known in the art of preparations.

Hereafter the examples of the present invention and reference examples are given.

Physicochemical properties shown in the following examples and reference examples were determined by the following apparatuses and devices.

| NMR | JEOL Ltd. | FX-100 (100 MHz) |
| --- | --- | --- |
| | JEOL Ltd. | PS-100 (100 MHz) |
| | Bruker | AM-400 (400 MHz) |
| MS | Hitachi Ltd. | M-80B |
| | Shimadzu Seisakusho Ltd. | QP-1000 |
| IR | Japan Spectral Co., Ltd. | IR-810 |

As silica gel, WAKO GEL C-200 ™ manufactured by Wako Pure Chemical Industry Co., Ltd. was used.

In the following examples and reference examples, treatment in a conventional manner refers to the treatment as described below.

Citrate or phosphate buffer of pH 5 is added to the reaction solution and the mixture is extracted with ethyl acetate or chloroform. The organic solvent layer is washed with saturated sodium chloride aqueous solution. After drying over anhydrous sodium sulfate, the solvent is evaporated under reduced pressure.

EXAMPLE 1 SYNTHESIS OF COMPOUND 1

After 142 mg (0.276 mmol) of Compound b was dissolved in 7 ml of pyridine, 0.25 ml (2.76 mmols) of dimethylcarbamoyl chloride was dropwise added to the solution with stirring under ice cooling. The mixture was stirred at 20° C. for 2 hours. The crude product obtained by treatment in a conventional manner was purified by silica gel column chromatography (silica gel, 20 ml; eluate; hexane:ethyl acetate=1:2) to give 120 mg (yield, 72.4%) of Compound 1.

Physicochemical properties of Compound 1 are as follows.

$^1$H-NMR (CDCl$_3$) δ (ppm); 8.49(1H, brs), 7.78(1H, d, J=15.3Hz), 7.55(2H, d, J=8.7Hz), 6.93(2H, d, J=8.7Hz), 6.69(1H, d, J=15.3Hz), 5.50(1H, brs), 4.41(1H, dd, J=10.7, 10.7Hz), 4.34(1H, dd, J=4.4, 10.7Hz), 4.19(1H, m), 4.04(1H, dd, J=3.2, 10.0Hz), 3.86(3H, s), 3.77(3H, s), 3.57(1H, dd, J=9.5, 9.5Hz), 3.14(3H, s), 3.05(3H, s), 1.67(3H, s)

SIMS (m/z); 586, 588(M+1)+

EXAMPLE 2 SYNTHESIS OF COMPOUND 2

In a manner similar to Example 1 except for using Compound c in place of Compound b, 87.3 mg (yield, 95.0%) of Compound 3 was obtained from 79.2 mg of Compound b.

Physicochemical properties of Compound 2 are as follows.

$^1$H-NMR (CDCl$_3$) δ (ppm); 8.48(1H, brs), 7.55(2H, d, J=9.5Hz), 7.44(2H, d, J=9.5Hz), 7.76(1H, d, J=15.3Hz), 6.78(1H, s), 6.74(1H, d, J=15.3Hz), 5.50(1H, s), 4.41(1H, dd, J=9.5, 10.0Hz), 4.34 (1H, dd, J=4.0, 10.0Hz), 4.19(1H, m), 4.02(1H, dd, J=3.0, 10.1Hz), 3.80(3H, s), 3.77(3H, s), 3.58 (1H, dd, J=10.1, 10.0Hz), 3.14(3H, s), 3.05(3H, s), 1.67(3H, s)

SIMS (m/z); 629, 631(M+1)+

EXAMPLE 3 SYNTHESIS OF COMPOUND 3

In a manner similar to Example 1 except for using Compound f in place of Compound b, 22.0 mg (yield, 48.6%) of Compound 3 was obtained from 40.0 mg of Compound f.

Physicochemical properties of Compound 3 are as follows.

$^1$H-NMR (CDCl$_3$) δ (ppm); 9.29(1H, brs), 8.63(1H, brs), 7.82(1H, d, J=1.0Hz), 7.73(2H, m), 7.66(1H, dd, J=0.8, 8.5Hz), 7.54(1H, m), 7.37(2H, m), 7.24 (1H, dd, J=2.1, 8.8Hz), 6.98(1H, d, J=1.4Hz), 6.32(1H, brs), 5.32(1H, brs), 4.68(1H, dd, J=10.7Hz), 4.62(1H, dd, J=4.5, 10.7Hz), 4.28(1H, m), 4.06(1H, dd, J=3.4, 10.1Hz), 3.79(3H, s), 3.62(1H, dd, J=8.6, 10.1Hz), 3.06(6H, s), 1.70 (3H, s)

SIMS (m/z); 728, 730(M+1)+

EXAMPLE 4 SYNTHESIS OF COMPOUND 4

In a manner similar to Example 1 except for using Compound g in place of Compound b, 100 mg (yield, 88.9%) of Compound 4 was obtained from 100 mg of Compound g.

Physicochemical properties of Compound 4 are as follows.

$^1$H-NMR (CDCl$_3$) δ (ppm); 8.48(1H, br), 8.05(1H, dd, J=11.6, 15.2Hz), 6.77(3H, m), 5.97(1H, d, J=11.3Hz), 5.47(1H, br), 4.31(1H, dd, J=10.7, 10.7Hz), 4.24(1H, dd, J=4.2, 10.7Hz), 4.13(1H, m), 4.01(1H, dd, J=10.0, 3.1Hz), 3.94(3H, s), 3.90(3H, s), 3.77(3H, s), 3.55(1H, dd, J=10.0, 10.0Hz), 3.15(3H, s), 3.05(3H, s), 1.67(3H, s)

SIMS (m/z); 642, 644(M+1)+

EXAMPLE 5 SYNTHESIS OF COMPOUND 5

In a manner similar to Example 1 except for using Compound h in place of Compound b, 34.3 mg (yield, 46.2%) of Compound 5 was obtained from 40 mg of Compound h.

Physicochemical properties of Compound 5 are as follows.

$^1$H-NMR (CDCl$_3$) δ (ppm); 9.32(1H, br), 8.48(1H, br), 8.24(1H, br), 7.78(1H, d, J=15.3Hz), 7.68(1H, dd, J=7.2, 0.9Hz), 7.70(2H, d, J=8.7Hz), 7.58(2H, d, J=8.7Hz), 7.45(1H, dd, J=0.9, 8.3Hz), 7.33(1H, ddd, J=1.1, 7.1, 7.1Hz), 7.17(1H, ddd, J=0.9, 7.1, 7.1Hz), 7.09(1H, dd, J=0.7, 2.0Hz), 6.73 (1H, d, J=15.3Hz), 5.41(1H, s), 4.37(1H, dd, J=10.2, 10.2Hz), 4.25(1H, dd, J=10.2, 4.6Hz), 4.12 (1H, m), 4.02(1H, dd, J=3.3, 10.1Hz), 3.76(3H, s), 3.50(1H, dd, J=10.1, 10.1Hz), 3.14(3H, s), 3.07 (3H, s), 1.56(3H, s)

SIMS (m/z); 714, 716(M+1)+

EXAMPLE 6 SYNTHESIS OF COMPOUND 6

In a manner similar to Example 1 except for using Compound i in place of Compound b, 44 mg (yield, 77.0%) of Compound 6 was obtained from 50 mg of Compound i.

Physicochemical properties of Compound 6 are as follows.

$^1$H-NMR (CDCl$_3$) δ (ppm); 8.33(1H, br), 6.93(2H, d, J=9.1Hz), 6.84(2H, d, J=9.1Hz), 5.48(1H, br), 4.73 (1H, d, J=14.1Hz), 4.72(1H, d, J=14.1Hz), 4.29 (2H, m), 4.15(1H, m), 3.95(1H, dd, J=3.4, 10.1Hz), 3.76(3H, s), 3.75(3H, s), 3.57(1H, dd, J=10.1, 8.8Hz), 3.12(3H, s), 3.03(3H, s), 1.66(3H, s)

EIMS (m/z); 589, 591(M+)

EXAMPLE 7 SYNTHESIS OF COMPOUND 7

While stirring, 16.2 μl (0.116 mmol) of triethylamine and 29.3 mg (0.146 mmol) of p-nitrophenyl chloroformate were added to 5 ml of dichloromethane solution of 30 mg (0.0582 mmol) of Compound b under ice cooling. The mixture was stirred at 0° C. for an hour and 19.4 μl (0.175 mmol) of N-methylpiperazine was added to the mixture. The mixture was stirred at 0° C. for further an hour. The crude product obtained by treatment in a conventional manner was purified by silica gel column chromatography (silica gel, 20 ml; eluate; chloroform:methanol=30:1) to give 27.5 mg (yield, 73.7%) of Compound 7.

The physicochemical properties of Compound 7 are shown below.

$^1$H-NMR (CDCl$_3$) δ (ppm); 8.49(1H, br), 7.78(1H, d, J=15.3Hz), 7.55(2H, d, J=8.7Hz), 6.93(2H, d, J=8.7Hz), 6.68(1H, d, J=15.3Hz), 5.46(1H, brs), 4.41(1H, dd, J=10.3, 10.3Hz), 4.34(1H, dd, J=4.4, 10.3Hz), 4.18(1H, m), 4.03(1H, dd, J=3.3, 9.3Hz), 3.86(3H, s), 3.78(2H, br), 3.77(3H, s), 3.65(2H, br), 3.59(1H, dd, J=9.3, 9.3Hz), 2.53 (4H, br), 2.39(3H, s), 1.67(3H, s)

SIMS (m/z); 641, 643(M+1)$^+$

EXAMPLE 8 SYNTHESIS OF COMPOUND 8

In a manner similar to Example 7 except for using piperidine in place of N-methylpiperazine, 43 mg (yield, 88.4%) of Compound 8 was obtained from 40 mg of Compound b.

The physicochemical properties of Compound 8 are shown below.

$^1$H-NMR (CDCl$_3$) δ (ppm); 8.48(1H, br), 7.78(1H, d, J=15.3Hz), 7.55(2H, d, J=8.7Hz), 6.93(2H, d, J=8.7Hz), 6.70(1H, d, J=15.3Hz), 5.50(1H, br), 4.41(1H, dd, J=10.5, 10.5Hz), 4.34(1H, dd, J=4.4, 10.5Hz), 4.19(1H, m), 4.04(1H, dd, J=3.3, 10.0Hz), 3.86(3H, s), 3.77(3H, s), 3.64(2H, br), 3.57(1H, dd, J=10.0, 10.0Hz), 3.53(2H, br), 1.67 (6H, br), 1.57(3H, s)

SIMS (m/z); 626, 628(M+1)$^+$

EXAMPLE 9 SYNTHESIS OF COMPOUND 9

In a manner similar to Example 7 except for using morpholine in place of N-methylpiperazine, 42 mg (yield, 86.1%) of Compound 9 was obtained from 40 mg of Compound b.

The physicochemical properties of Compound 9 are shown below.

$^1$H-NMR (CDCl$_3$) δ (ppm); 8.50(1H, br), 7.78(1H, d, J=15.3Hz), 7.55(2H, d, J=8.7Hz), 6.93(2H, d, J=8.7 Hz), 6.69(1H, d, J=15.3Hz), 5.45(1H, br), 4.42 (1H, dd, J=10.5, 10.5Hz), 4.34(1H, dd, J=4.4, 10.5Hz), 4.19(1H, m), 4.03(1H, dd, J=3.4, 10.0Hz), 3.86(3H, s), 3.77(3H, s), 3.76(4H, br), 3.72(2H, br), 3.60(2H, br), 3.59(1H, dd, J=10.0, 9.0Hz), 1.67(3H, s)

SIMS (m/z); 628, 630(M+1)$^+$

EXAMPLE 10 SYNTHESIS OF COMPOUND 10

In a manner similar to Example 1 except for using Compound j in place of Compound b, 36 mg (yield, 68%) of Compound 10 was obtained from 47 mg of Compound j.

The physicochemical properties of Compound 10 are shown below.

$^1$H-NMR (CDCl$_3$) δ (ppm); 9.40(1H, br), 8.43(1H, s), 7.82(1H, br), 7.37(1H, d, J=8.8Hz), 7.21(1H, dd, J=8.8, 1.7Hz), 6.98(1H, brs), 6.65(1H, brs), 5.53(1H, brs), 4.62(1H, dd, J=10.6, 9.4Hz), 4.57 (1H, dd, J=10.7, 4.5Hz), 4.23(1H, m), 4.02(1H, dd, J=10.1, 3.4Hz), 3.80(3H, s), 3.79(3H, s), 3.62(1H, dd, J=10.0, 8.7Hz), 3.14(3H, s), 3.05 (3H, s), 1.68(3H, s)

EXAMPLE 11 SYNTHESIS OF COMPOUND 11

In a manner similar to Example 1 except for using Compound k in place of Compound b, 23 mg (yield, 96%) of Compound 11 was obtained from 21 mg of Compound k.

Physicochemical properties of Compound 11 are as follows.

$^1$H-NMR (CDCl$_3$) δ (ppm); 8.49(1H, br), 7.76(1H, d, J=15.2Hz), 7.49(2H, d, J=8.9Hz), 6.69(2H, d, J=8.9 Hz), 6.59(1H, d, J=15.2Hz), 5.50(1H, brs), 4.40 (1H, dd, J=10.6, 9.6Hz), 4.33(1H, dd, J=10.7, 4.4Hz), 4.18(1H, m), 4.03(1H, dd, J=9.9, 3.3Hz), 3.76(3H, s), 3.56(1H, dd, J=9.6, 9.5Hz), 3.14 (3H, s), 3.04(3H, s), 1.67(3H, s)

EXAMPLE 12 SYNTHESIS OF COMPOUND 12

Compound 12 (29.5 mg; yield: 85.0%) was obtained from 30 mg of Compound 1 in the same way as in Example 1 except that Compound 1 was used in place of Compound b.

The physicochemical properties of Compound 12 are shown below.

$^1$H-NMR (CDCl$_3$) δ (ppm); 8.31(1H, br), 7.74(2H, d, J=8.8Hz), 7.69(1H, s), 7.56(1H, d, J=15.3Hz), 6.99(1H, d, J=15.3Hz), 6.98(2H, d, J=8.8Hz), 4.51(1H, dd, J=10.5, 10.5Hz), 4.33(1H, dd, J=4.5, 10.5Hz), 4.13(1H, m), 4.05(1H, dd, J=3.2, 10.8Hz), 3.99(1H, dd, J=7.1, 10.8Hz), 3.81(3H, s), 3.62 (3H, s), 3.10(3H, s), 2.95(3H, s), 1.47(3H, s)

SIMS (m/z); 542(M+1)$^+$

EXAMPLE 13 SYNTHESIS OF COMPOUND 13

Compound 13 (41 mg; yield 89%) was obtained from 40 mg of Compound m in the same way as in Example 1 except that Compound m was used in place of Compound b.

The physicochemical properties of Compound 13 are shown below.

$^1$H-NMR (CDCl$_3$) δ (ppm); 8.30(1H, br), 7.68(1H, s), 7.58(2H, d, J=8.9Hz), 7.51(1H, d, J=15.2Hz), 6.80(1H, d, J=15.2Hz), 6.72(2H, d, J=8.9Hz), 4.48(1H, dd, J=10.4, 10.4Hz), 4.29(1H, dd, J=4.6, 10.4Hz), 4.12(1H, m), 4.03(2H, m), 3.62(3H, s), 3.10(3H, s), 2.97(6H, s), 2.92(3H, s), 1.47(3H, s)

SIMS (m/z); 555(M+1)$^+$

EXAMPLE 14 SYNTHESIS OF COMPOUND 14

Compound 14 (71.3 mg; yield 94.0%) was obtained from 60 mg of Compound 1 in the same way as in Example 7 except that Compound 1 was used in place of Compound b.

The physicochemical properties of Compound 14 are shown below.

$^1$H-NMR (CDCl$_3$) δ (ppm); 8.33(1H, s), 7.73(2H, d, J=9.2Hz), 7.66(1H, s), 7.57(1H, d, J=15.3Hz), 7.00(1H, d, J=15.3Hz), 6.99(2H, d, J=9.2Hz), 4.51(1H, dd, J=10.5, 10.5Hz), 4.33(1H, dd, J=4.5, 10.5Hz), 4.14(1H, m), 4.05(1H, dd, J=2.9, 10.7Hz), 3.99(1H, dd, J=7.0, 10.7Hz), 3.81(3H, s), 3.63(2H, m), 3.32(3H, s), 3.46(2H, m), 2.40 (4H, m), 2.23(3H, s), 1.49(3H, s)

SIMS (m/z); 597(M+1)$^+$

EXAMPLE 15 SYNTHESIS OF COMPOUND 15

60% Sodium hydride (8.7 mg; 0.218 mmol) was suspended in 0.8 ml of dimethylformamide under an argon atmosphere. The suspension thus obtained was cooled to −40° C., and a solution of Compound a (50 mg; 0.182 mmol) in 1 ml of dimethylformamide was dropwise added to the cooled suspension. The mixture was stirred for two hours at a temperature of between −40° C. and −20° C. and then cooled to −50° C. A solution of 98 mg (0.237 mmol) p-nitrophenyl 4-(N-t-butoxycarbonyl-methylamino)cinnamate in 3 ml of dimethylformamide was dropwise added, and stirring was continued for 50 minutes at a temperature of between −50° C. and −30° C. After adding 0.08 ml of 47%-hydrobromic acid, stirring was further continued for 20 minutes, and the reaction mixture was worked up according to the conventional manner, to obtain 180 mg of a crude product.

To a solution of the crude product (135 mg) in 4 ml of pyridine was added with stirring 0.126 ml (1.37 mmol) of dimethylcarbamoyl chloride under ice cooling. Stirring was continued at room temperature for 7 hours, and the reaction mixture was worked up according to conventional manner, to obtain 150 mg of a crude product. To a solution of the crude product (150 mg) in 2 ml of dichloromethane was added 1 ml of trifluoroacetic acid, and the mixture was stirred at room temperature for 10 minutes and concentrated under reduced pressure. The crude product thus obtained was purified by silica gel column chromatography (silica gel, 120 ml; eluate; chloroform:acetone=30:1), to afford 57.3 mg (71.7%) of Compound 15.

The physicochemical properties of Compound 15 are shown below.

$^1$H-NMR (CDCl$_3$) δ (ppm); 8.47(1H, br), 7.75(1H, d, J=15.2Hz), 7.48(2H, d, J=8.5Hz), 7.22(1H, s), 6.72 (2H, d, J=8.5Hz), 6.61(1H, d, J=15.2Hz), 4.39(1H, dd, J=10.2, 10.2Hz), 4.31(1H, dd, J=4.4, 10.2Hz), 4.17(1H, m), 4.02(1H, dd, J=3.2, 10.0Hz), 3.78 (1H, br), 3.78(3H, s), 3.57(1H, dd, J=10.0, 10.0 Hz), 3.15(3H, s), 3.05(3H, s), 2.91(3H, s), 1.67 (3H, s)

SIMS (m/z); 585, 587(M+1)+

EXAMPLE 16 SYNTHESIS OF COMPOUND 16

60% Sodium hydride (8.7 mg; 0.218 mmol) was suspended in 0.8 ml of dimethylformamide under an argon atmosphere. The suspension was cooled to −40° C., and a solution of Compound a (50 mg; 0.182 mmol) in 1 ml of dimethylformamide was dropwise added to the cooled suspension. The mixture was stirred for 2 hours at a temperature of −40° C. and −20° C. and then cooled to −50° C. A solution of 74.1 mg (0.237 mmol) of p-nitrophenyl benzofuran-2-carboxylate in 2 ml of dimethylformamide was dropwise added and stirring was continued for 50 minutes at a temperature of between −50° C. and −30° C. After adding 0.08 ml of 47% hydrobromic acid, stirring was further continued for 20 minutes. The reaction mixture was worked up according to the conventional manner, to obtain 140 mg of a crude product. To a solution of the crude product (140 mg) in 6 ml of pyridine, was added with stirring 0.168 ml (1.82 mmol) of dimethylcarbamoyl chloride under ice cooling, and stirring was continued at room temperature for 7 hours. The reaction mixture was worked up according to the conventional manner. The crude product thus obtained was purified by silica gel column chromatography (silica gel, 30 ml; eluate; chloroform:methanol=20:1), to afford 45.6 mg (41.0%) of Compound 16.

The physicochemical properties of Compound 16 are shown below.

$^1$H-NMR (CDCl$_3$) δ (ppm); 8.43(1H, br), 7.52(1H, d, J=0.9Hz), 7.49(1H, d, J=9.0Hz), 7.11(1H, d, J=2.4Hz), 7.07(1H, dd, J=9.0, 2.4Hz), 5.50(1H, br), 4.71(2H, m), 4.22(1H, m), 3.98(1H, dd, J=3.3, 10.1Hz), 3.87(3H, s), 3.78(3H, s), 3.66(1H, dd, J=8.4, 10.1Hz), 3.15(3H, s), 3.05(3H, s), 1.88(3H, s)

SIMS (m/z); 600, 602(M+1)+

EXAMPLE 17 SYNTHESIS OF COMPOUND 17

60% Sodium hydride (8.7 mg; 0.218 mmol) was suspended in 0.8 ml of dimethylformamide under an argon atmosphere, and the suspension was cooled to −40° C. A solution of Compound a (50 mg; 0.182 mmol) in 1 ml of dimethylformamide was dropwise added to the cooled suspension. The mixture was stirred for 2 hours at a temperature of between −40° C. and −20° C. and then cooled to −50° C., a solution of 90.5 mg (0.218 mmol) p-nitrophenyl (3-t-butoxycarbonylamino-4-methoxy)cinnamate in 3 ml of dimethylformamide was dropwise added, and stirring was continued for 50 minutes at a temperature of between −50° C. and −30° C. After adding 0.08 ml of 47%-hydrobromic acid, stirring was further continued for 20 minutes, and the reaction mixture was worked up according to the conventional manner, to give 160 mg of a crude product. To a solution of the crude product (120 mg) in 5 ml of pyridine, was added with stirring 0.24 ml (2.61 mmol) of dimethylcarbamoyl chloride under ice cooling, stirring was continued at room temperature for 7 hours, and the reaction mixture was worked up according to the conventional manner, to give 400 mg of a crude product. TO a solution of the crude product (400 mg) in 8 ml of dichloromethane, was added 3 ml of trifluoroacetic acid, and the mixture was stirred at room temperature for 30 minutes and concentrated under reduced pressure. The crude product thus obtained was purified by silica gel column chromatography (silica gel, 30 ml; eluate; chloroform:methanol=50:1), to afford 53.6 mg (73.5%) of Compound 17.

The physicochemical properties of Compound 17 are shown below.

$^1$H-NMR (CDCl$_3$) δ (ppm); 8.47(1H, br), 7.68(1H, d, J=15.3Hz), 7.08(1H, br), 7.07(1H, d, J=8.3Hz), 6.81(1H, d, J=8.3Hz), 6.63(1H, d, J=15.3Hz), 4.38(1H, dd, J=10.6, 10.6Hz), 4.32(1H, dd, J=10.6, 4.4Hz), 4.41(1H, m), 4.00(1H, dd, J=3.4, 10.0Hz), 3.89(3H, s), 3.78(3H,s), 3.77(1H, m), 3.75(2H, br), 3.58(1H, dd, J=10.0, 10.0Hz), 3.15 (3H, s), 3.05(3H, s), 1.67(3H, s)

SIMS (m/z); 601, 603(M+1)+

REFERENCE EXAMPLE 1 SYNTHESIS OF COMPOUND a

After 93 mg (0.18 mmol) of DC-88A was dissolved in 10 ml of methanol, 70 μl of methanol solution of 28% sodium methoxide was dropwise added to the solution under ice cooling. After completion of the dropwise addition, the mixture was stirred for 40 minutes under ice cooling. Then 0.1M phosphate buffer (pH 5.3) was added to the reaction mixture and methanol was evaporated. After adding sodium chloride, the mixture was extracted 3 times with ethyl acetate-THF. After drying over anhydrous sodium sulfate, the extract was concentrated under reduced pressure. The residue was purified by silica gel column chromatography (silica gel, 12 ml; eluate; chloroform:acetone=1:0 to 3:1) to give 49 mg (yield, 97%) of Compound a.

Physicochemical properties of Compound a are as follows.

$^1$H-NMR (CDCl$_3$) δ (ppm); 6.16(1H, brs), 5.74(1H, s), 5.46(1H, brs), 3.81(1H, ddd, J=11.0, 5.6, 1.5Hz), 3.73(3H, s), 3.69(1H, d, J=11.0Hz), 3.03(1H, m), 2.05(1H, dd, J=7.8, 3.5Hz), 1.63(3H, s), 1.01(1H, dd, J=4.6, 3.5Hz)

IR (CHCl$_3$) cm$^{-1}$; 3450, 1740, 1685, 1560

SIMS (m/z); 275(M+1)+

REFERENCE EXAMPLE 2 SYNTHESIS OF COMPOUND b

In an argon atmosphere, 17.5 mg (0.44 mmol) of 60% sodium hydride was suspended in 1.6 ml of dimethylformamide. The suspension was cooled to −40° C. and dimethylformamide solution (2 ml) of 100 mg (0.37 mmol) of Compound a was dropwise added to the suspension. The mixture was stirred at −40° to −20° C. for 2 hours and then cooled to −50° C. Then, 6 ml of dimethylformamide solution of 153 mg (0.51 mmol) of p-nitrophenyl 4-methoxycinnamate was dropwise added to the mixture. After stirring at −50° to −30° C. for 50 minutes, 0.16 ml of 47% hydrobromic acid aqueous solution was added thereto followed by stirring for further 20 minutes. The crude product obtained by treatment in a conventional manner was purified by silica gel column chromatography (silica gel, 80 ml; eluate; chloroform:acetone=10:1) to give 150 mg (yield, 78.3%) of Compound b.

Physicochemical properties of Compound b are as follows.

$^1$H-NMR (CDCl$_3$) δ (ppm); 10.84(1H, brs), 8.59(1H, s), 7.76(1H, d, J=15.5Hz), 7.58(2H, d, J=8.8Hz), 6.94(2H, d, J=8.8Hz), 6.73(1H, d, J=15.5Hz), 5.31(1H, s), 4.39(1H, dd, J=10.6, 9.5Hz), 4.28 (1Hd, dd, J=10.7, 4.3Hz), 4.08(1H, m), 4.04(1H, dd, J=9.6, 3.2Hz), 3.87(3H, s), 3.78(3H, s), 3.55(1H, dd, J=9.6, 8.9Hz), 1.69(3H, s)

EIMS (m/z); 514, 516(M+), 434(M-HBr)+, 375(M-HBr-CO$_2$CH$_3$)+, 354, 356, 161, 133

IR (KRr) cm$^{-1}$; 3354, 1742, 1698, 1635, 1602, 1508, 1434, 1305, 1251, 1173

REFERENCE EXAMPLE 3 SYNTHESIS OF COMPOUND c

In a manner similar to Reference Example 2 except for using p-nitrophenyl 4-methoxycarbonylaminocinnamate in place of p-nitrophenyl 4-methoxycinnamate, 80 mg (yield, 78.4%) of Compound c was obtained from 50 mg of Compound a.

Physicochemical properties of Compound c are as follows.

$^1$H-NMR (DMSO-d$_6$) δ (ppm); 10.15(1H, br), 9.85(1H, s), 8.15(1H, s), 7.70(2H, d, J=8.7Hz), 7.52(2H, d, J=8.7Hz), 7.27(1H, s), 6.99(1H, d, J=15.3Hz), 4.46(1H, dd, J=10.6, 10.6Hz), 4.19(1H, dd, J=4.7, 10.6Hz), 4.06(1H, m), 3.30(1H, dd, J=2.9, 9.8Hz), 3.79(1H, dd, J=7.7, 9.8Hz), 3.69(3H, s), 3.59(3H, s), 1.45(3H, s)

REFERENCE EXAMPLE 4 SYNTHESIS OF COMPOUND f

In an argon atmosphere, 17.5 mg (0.44 mmol) of 60% sodium hydride was suspended in 1.6 ml of dimethylformamide. The suspension was cooled to −40° C. and 2 ml of dimethylformamide solution containing 100 mg (0.37 mmol) of Compound a was dropwise added to the suspension. The mixture was stirred at −40° to −20° C. for 2 hours and then cooled to −50° C. Then, 6 ml of dimethylformamide solution containing 203 mg (0.51 mmol) of p-nitrophenyl 5-(t-butoxycarbonyl)aminoindole-2-carboxylate was dropwise added to the mixture. After stirring at −50° to −30° C. for 50 minutes, the crude product obtained by treatment in a conventional manner was purified by silica gel column chromatography (silica gel, 80 ml; eluate; chloroform:acetone=10:1) to give 113 mg (yield, 58.0%) of Compound d.

Physicochemical properties of Compound d are as follows.

$^1$H-NMR (DMSO-d$_6$) δ (ppm); 11.68(1H, brs), 9.16(1H, br), 8.70(1H, s), 7.79(1H, brs), 7.34(2H, br), 7.12(1H, d, J=2.0Hz), 6.93(1H, s), 4.57(1H, dd, J=10.6, 5.3Hz), 4.43(1H, d, J=10.6Hz), 3.61(3H, s), 3.01(1H, m), 1.96(1H, dd, J=7.6, 3.6Hz), 1.49(9H, s), 1.46(3H, s), 1.43(1H, dd, J=4.8, 3.8Hz)

SIMS (m/z); 535(M+3)+, 479

After 113 mg of Compound d was dissolved in acetonitrile, 0.13 ml of 47% hydrobromic acid aqueous solution was dropwise added to the solution at room temperature while stirring. The mixture was stirred at room temperature for 3 hours. The crude product obtained by treatment in a conventional manner was purified by silica gel column chromatography (silica gel, 50 ml; eluate; chloroform:acetone=10:1) to give 101 mg (yield, 92%) of Compound e.

Physicochemical properties of Compound e are as follows.

$^1$H-NMR (DMSO-d$_6$) δ (ppm); 11.21(1H, brs), 10.17(1H, s), 8.07(1H, brs), 7.31(1H, s), 7.20(1H, d, J=8.7Hz), 6.81(1H, d, J=1.7Hz), 6.77(1H, d, J=1.8Hz), 6.68 (1H, dd, J=8.7, 2.1Hz), 4.79(2H, br), 4.65(1H, dd, J=10.8, 9.7Hz), 4.33(1H, dd, J=11.0, 4.2Hz), 4.07(1H, m), 3.93(1H, dd, J=9.6, 2.8Hz), 3.82 (1H, dd, J=9.7, 7.2Hz), 3.61(3H, s), 1.47(3H, s)

SIMS (m/z); 513, 515(M+1)+

After 100 mg (0.195 mmol) of Compound e was dissolved in acetonitrile, 83.5 mg (0.293 mmol) of p-nitrophenyl benzofuran-2-carboxylate and 4 mg of 4-dimethylaminopyridine were added to the solution at room temperature with stirring. After stirring at room temperature for 16 hours, the crude product obtained by treatment in a conventional manner was purified by silica gel column chromatography (silica gel, 50 ml; eluate; chloroform:acetone=10:1) to give 40 mg (yield, 30%) of Compound f.

Physicochemical properties of Compound f are as follows.

$^1$H-NMR (CDCl$_3$) δ (ppm); 9.23(1H, br), 8.64(1H, s), 7.81(1H, d, J=0.9Hz), 7.77(1H, m), 7.65(1H, dd, J=8.5, 0.8Hz), 7.54(1H, ddd, J=8.4, 7.3, 1.3Hz), 7.38(1H, ddd, J=8.0, 7.3, 0.9Hz), 7.27(1H, d, J=8.6Hz), 6.96(1H, d, J=2.1Hz), 6.88(1H, d, J=1.4Hz), 6.81(1H, d, J=8.7, 2.2Hz), 5.32(1H, s), 4.66(1H, dd, J=10.8, 9.3Hz), 4.61(1H, dd, J=10.8, 4.6Hz), 4.26(1H, m), 4.05(1H, dd, J=10.1, 3.3Hz), 3.79(3H, s), 3.66(1H, dd, J=10.0, 8.7Hz), 1.70 (3H, s)

SIMS (m/z); 657, 659(M+1)+, 498, 500(M+1-CO$_2$CH$_3$)+

IR (KBr) cm$^{-1}$; 3370, 1741, 1629, 1521, 1491, 1411, 1293, 1170

REFERENCE EXAMPLE 5 SYNTHESIS OF COMPOUND g

In a manner similar to Reference Example 2 except for using p-nitrophenyl 5-(4-methoxyphenyl)-penta-2,4-dienoate in place of p-nitrophenyl 4-methoxycinnamate, 100 mg (yield, 96.2%) of Compound g was obtained from 50 mg of Compound a.

Physicochemical properties of Compound g are as follows.

$^1$H-NMR (CDCl$_3$) δ (ppm) 8.54(1H br) 7.68(1H dd, J=12.4, 15.4Hz), 7.06(3H, m), 6.79(4H, m), 6.01 (1H, d, J=1.3Hz), 4.29(1H, dd, J=11.0, 11.0Hz), 4.17(1H, dd, J=4.2, 11.0Hz), 4.11(1H, m), 3.99 (1H, dd, J=4.2, 9.0Hz), 3.86(3H, s), 3.73(3H, s), 3.70(3H, s), 3.60(1H, dd, J=9.0, 10.0Hz), 1.57 (3H, s)

REFERENCE EXAMPLE 6 SYNTHESIS OF COMPOUND h

In a manner similar to Reference Example 2 except for using p-nitrophenyl 4-(indole-2-carbonylamino)cinnamate in place of p-nitrophenyl 4-methoxycinnamate, 42.0 mg (yield, 35.9%) of Compound h was obtained from 50 mg of Compound a.

Physicochemical properties of Compound h are as follows.

$^1$H-NMR (DMSO-d$_6$) δ (ppm); 12.17(1H, brs), 8.50(1H, brs), 7.93(1H, s), 7.74(1H, d, J=7.9Hz), 7.46–7.54(3H, m), 7.45(2H, d, J=8.5Hz), 7.33(1H, t, J=7.2Hz), 7.14(1H, t, J=7.2Hz), 6.75(1H, d, J=15.2Hz), 6.58(2H, d, J=8.5Hz), 5.69(2H, brs), 4.53(1H, dd, J=10.0, 9.9Hz), 4.27(1H, m), 4.23 (1H, m), 3.96(2H, m), 3.62(3H, s), 1.48(3H, s)

SIMS (m/z); 643, 645(M+1)$^+$

IR (KBr) cm$^{-1}$; 3364, 1733 (br), 1635, 1594, 1516, 1490, 1433, 1309, 1263, 1175, 1144

REFERENCE EXAMPLE 7 SYNTHESIS OF COMPOUND i

In a manner similar to Reference Example 2 except for using p-nitrophenyl 4-methoxyphenoxyacetate in place of p-nitrophenyl 4-methoxycinnamate, 57.0 mg (yield, 60.3%) of Compound i was obtained from 50 mg of Compound a.

Physicochemical properties of Compound i are as follows.

$^1$H-NMR (DMSO-d$_6$) δ (ppm); 7.95(1H, s), 6.93(2H, d, J=9.2Hz), 6.85(2H, d, J=9.2Hz), 4.72(2H, s), 4.24 (1H, dd, J=9.4, 11.0Hz), 4.16(1H, dd, J=4.1, 11.0Hz), 4.09(1H, m), 3.96(1H, dd, J=3.3, 9.4Hz), 3.77(3H, s), 3.75(3H, s), 3.57(1H, dd, J=8.3, 9.4Hz), 1.66(3H, s)

REFERENCE EXAMPLE 8 SYNTHESIS OF COMPOUND j

In a manner similar to Reference Example 2 except for using p-nitrophenyl 5-methoxycarbonylaminoindole-2-carboxylate in place of p-nitrophenyl 4-methoxycinnamate, 47 mg (yield, 47%) of Compound j was obtained from 40 mg of Compound a.

Physicochemical properties of Compound j are as follows.

$^1$H-NMR (DMSO-d$_6$) δ (ppm); 11.55(1H, d, J=1.7Hz), 10.19 (1H, s), 9.43(1H, br), 8.07(1H, br), 7.79(1H, br), 7.38(1H, d, J=8.8Hz), 7.33(1H, s), 7.27(1H, dd, J=8.8, 1.7Hz), 7.04(1H, d, J=1.7Hz), 4.68(1H, dd, J=10.8, 10.8Hz), 4.35(1H, dd, J=4.2, 10.8Hz), 4.08(1H, m), 3.93(1H, dd, J=9.8, 3.0Hz), 3.83 (1H, dd, J=9.8, 7.1Hz), 3.66(3H, s), 3.61(3H, s), 1.47(3H, s)

REFERENCE EXAMPLE 9 SYNTHESIS OF COMPOUND k

In a manner similar to Reference Example 2 except for using 2,4,5-trichlorophenyl 4-dimethylaminocinnamate in place of p-nitrophenyl 4-methoxycinnamate, 28.2 mg (yield, 58.6%) of Compound k was obtained from 25 mg of Compound a.

Physicochemical properties of Compound k are as follows.

$^1$H-NMR (DMSO-d$_6$) δ (ppm); 10.11(1H, brs), 8.17(1H, br), 7.58(2H, d, J=8.9Hz), 7.52(1H, d, J=15.2Hz), 7.22 (1H, brs), 6.80(1H, d, J=15.2Hz), 6.73(2H, d, J=8.9Hz), 4.45(1H, dd, J=10.1, 10.0Hz), 4.18(1H, dd, J=10.9, 4.4Hz), 4.05(1H, m), 3.91(1H, dd, J=9.7, 2.9Hz), 3.79(1H, dd, J=9.7, 7.6Hz), 3.60 (3H, s), 2.99(6H, s), 1.46(3H, s)

EIMS (m/z); 527, 529(M$^+$), 447(M-HBr)$^+$, 388(M-HBr-CO$_2$CH$_3$)$^+$, 174

REFERENCE EXAMPLE 10 SYNTHESIS OF COMPOUND l

Compound l 117 mg; 68.1%) was obtained from 100 mg of Compound a in the same way as in Reference Example 2 except that 36%-Hydrochloric acid was used in place of 47%-Hydrobromic acid.

The physicochemical properties of Compound l are shown below.

$^1$H-NMR (CDCl$_3$) δ (ppm); 10.1(1H, s), 8.16(1H, s), 7.73(2H, d, J=8.8Hz), 7.56(1H, d, J=13.9Hz), 7.26(1H, s), 6.99(2H, d, J=8.8Hz), 6.98(1H, d, J=13.9Hz), 4.45(1H, dd, J=10.4, 10.4Hz), 4.27 (1H, dd, J=4.1, 10.4Hz), 4.02(2H, m), 3.89(1H, dd, J=8.2, 11.0Hz), 3.81(3H, s), 3.59(3H, s), 1.45(3H, s)

SIMS (m/z); 471(M+1)$^+$

REFERENCE EXAMPLE 11 SYNTHESIS OF COMPOUND m

Compound m (41.0 mg; yield 89%) was obtained from 50 mg of Compound a in the same way as in Reference Example 10 except that 2,4,5-trichlorophenyl 4-dimethylaminocinnamate was used in place of p-nitrophenyl p-methoxycinnamate.

The physicochemical properties of Compound m are shown below.

$^1$H-NMR (DMSO-d$_6$) δ (ppm); 10.12(1H, br), 8.16(1H, br), 7.94(1H, s), 7.59(2H, d, J=8.9Hz), 7.52(1H, d, J=15.2Hz), 6.81(1H, d, J=15.2Hz), 6.74(2H, d, J=8.9Hz), 4.43(1H, dd, J=10.3, 10.3Hz), 4.23(1H, dd, J=4.0, 10.3Hz), 4.00(1H, dd, J=2.8, 11.0Hz), 3.91(1H, m), 3.87(1H, dd, J=5.5, 11.0Hz), 3.59 (3H, s), 2.89(3H, s), 2.73(3H, s), 1.45(3H, s)

SIMS (m/z); 484(M+1)$^+$

According to the present invention, there are provided DC-89 derivatives having an excellent anti-tumor activity which are useful as the anti-tumor agent.

While the invention has been described in detail and with reference to specific embodiments thereof, it is apparent to one skilled in the art that various changes and modifications can be made therein without departing from the spirit and the scope of the present invention.

What is claimed is:

1. A DC-89 derivative represented by formula:

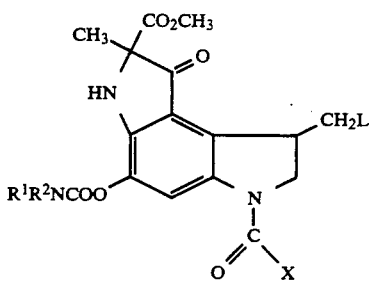

wherein L represents chlorine or bromine; each of R$^1$ and R$^2$ independently represents hydrogen, lower alkyl or phenyl; X represents a member selected from the group consisting of (a), (b) and (c) as follows:

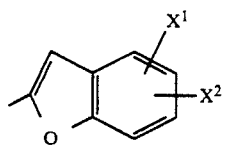

wherein each of $X^1$ and $X^2$ independently represents hydrogen, $OR^3$, $NHCO_2R^3$ (wherein $R^3$ represents lower alkyl) or $NR^4R^5$ (wherein each of $R^4$ and $R^5$ independently represents hydrogen or lower alkyl);

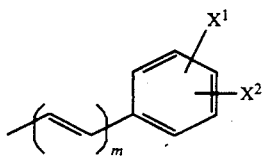

wherein m represents 1 or 2;

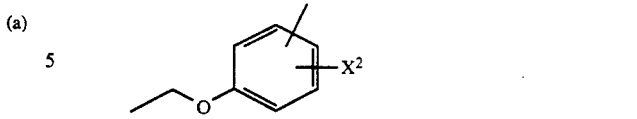

or a pharmaceutically acceptable salt thereof.

2. A compound according to claim 1, wherein X represents

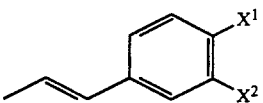

3. A compound according to claim 2 wherein $X^1$ represents methoxy, methylamino or dimethylamino and $X^2$ is hydrogen.

4. A compound according to claim 3, wherein L represents bromine.

5. A pharmaceutical composition which comprises a pharmaceutically acceptable carrier and, as an active ingredient, an effective amount of the DC-89 derivative as defined by claim 1.

* * * * *

UNITED STATES PATENT AND TRADEMARK OFFICE
CERTIFICATE OF CORRECTION

PATENT NO. : 5,214,065

DATED : May 25, 1993

INVENTOR(S) : HIROMITSU SAITO, ET AL.

It is certified that error appears in the above-identified patent and that said Letters Patent is hereby corrected as shown below:

COLUMN 2

Line 15, "$R^1R^2$" should read --$R^1R^2N$--.
Line 22, "7) or" should read --7), or--.
Line 32, "(e)." should read --(e):--.

COLUMN 3

Line 8, "(b);" should read --(b),--.
Line 9, "above." should read --above;--.

COLUMN 16

Line 54, "EIMS" should read --SIMS--.

COLUMN 20

Line 16, "TO" should read --To--.

COLUMN 21

Line 24, "(KRr)" should read --(KBr)--.

COLUMN 22

Line 57, "(ppm)" should read --(ppm);--;
"(1H br)" should read --(1H, br)--; and
"(1H dd," should read --(1H, dd,--.

COLUMN 24

Line 4, "117 mg;" should read --(117 mg;--.

UNITED STATES PATENT AND TRADEMARK OFFICE
CERTIFICATE OF CORRECTION

PATENT NO. : 5,214,065
DATED : May 25, 1993
INVENTOR(S) : HIROMITSU SAITO, ET AL.

It is certified that error appears in the above-identified patent and that said Letters Patent is hereby corrected as shown below:

COLUMN 26

Line 18, "claim 2" should read --claim 2,--.

Signed and Sealed this

Twenty-ninth Day of March, 1994

BRUCE LEHMAN

Attest:

Attesting Officer

Commissioner of Patents and Trademarks